(12) United States Patent
Yayama

(10) Patent No.: US 6,582,454 B2
(45) Date of Patent: Jun. 24, 2003

(54) LASER BEAM TREATMENT APPARATUS

(76) Inventor: Toshihiko Yayama, 159-13, Ogi-Machi, Ogi-Gun, Saga-Ken 845-0001 (JP)

( * ) Notice: Subject to any disclaimer, the term of this patent is extended or adjusted under 35 U.S.C. 154(b) by 1 day.

(21) Appl. No.: 09/737,472

(22) Filed: Dec. 18, 2000

(65) Prior Publication Data
US 2001/0007078 A1 Jul. 5, 2001

(30) Foreign Application Priority Data
Dec. 28, 1999 (JP) ........................................... 11-374252

(51) Int. Cl.$^7$ ............................................... A61B 17/00
(52) U.S. Cl. ....................................................... 607/89
(58) Field of Search ............................. 607/89, 90, 91, 607/92, 84, 85; 385/115, 4, 9; 359/298

(56) References Cited

U.S. PATENT DOCUMENTS

| | | | |
|---|---|---|---|
| 5,374,991 A | * 12/1994 | Atkinson et al. | ........... 356/358 |
| 5,415,978 A | * 5/1995 | Asami et al. | ................ 430/363 |
| 5,736,410 A | * 4/1998 | Zarling et al. | ............ 250/458.1 |
| 5,949,520 A | * 9/1999 | Heacock | ...................... 351/221 |
| 6,141,465 A | * 10/2000 | Bischel et al. | ................. 385/10 |
| 6,150,943 A | * 11/2000 | Lehman et al. | .............. 340/332 |
| 6,156,028 A | * 12/2000 | Prescott | ............................ 36/1 |
| 6,200,309 B1 | * 3/2001 | Rice et al. | ...................... 372/3 |
| 6,212,213 B1 | * 4/2001 | Weber et al. | ................... 257/88 |
| 6,226,126 B1 | * 5/2001 | Conemac | ...................... 250/230 |
| 6,312,451 B1 | * 11/2001 | Streeter | ......................... 606/11 |
| 6,364,487 B1 | * 4/2002 | Weber et al. | .................. 353/30 |

* cited by examiner

*Primary Examiner*—Teresa Walberg
*Assistant Examiner*—Daniel Robinson
(74) *Attorney, Agent, or Firm*—Rader, Fishman & Grauer PLLC

(57) ABSTRACT

A laser beam treatment apparatus includes a laser beam generating part generating and emitting a plurality of laser beams of different colors, and a projecting part condensing the plurality of laser beams and projecting the laser beams onto a treatment object region.

22 Claims, 4 Drawing Sheets

LASER BEAM TREATMENT APPARATUS

BACKGROUND OF THE INVENTION

1. Field of the Invention

The present invention relates to a laser beam treatment apparatus using a low-reactive level laser therapy (LLLT), and more particularly to a laser beam treatment apparatus that has improved safety and wider application ranges.

2. Description of the Related Art

FIGS. 1A and 1B are block diagrams schematically illustrating the overall structure of a conventional laser beam treatment apparatus. Referring to FIGS. 1A and 1B, the conventional laser beam treatment apparatus is made up of a laser beam generating part 100, a projecting part 200, a switch part 300, and a power supply part 400. The laser beam generating part 100 generates a single-color laser beam of a wavelength of approximately 670 nm in the red color range at a power level of 60 mW to 100 mW. The projecting part 200 condenses the single-color laser beam on a treatment object region 500 of a patient. The switch part 300 controls the output of the single-color laser beam emitted by the laser beam generating part 100. The power supply part 400 supplies a current to the laser beam generating part 100.

The projecting part 200 includes an optical system having an optical axis aligned in an outgoing direction of the laser beam generating part 100 in which the single-color laser beam travels. A front end part of the projecting part 200 is a focal plane when the switch part 300 is in an ON state. The switch part 300 has a probe 300a formed of a frame member which is slidably provided around an outer surface of the projecting part 200. When the probe 300a is pushed against the patient, the switch part 300 is turned ON, so that the laser beam generating part 100 is supplied with current from the power supply part 400. Thus, the single-color laser beam is projected onto the treatment object region 400.

A description will be given of a treatment operation of the conventional laser beam treatment apparatus thus configured. Before a treatment is initiated, the probe 300a of the switch part 300 protrudes from the projecting part 200, as shown in FIG. 1A. In this state, the switch 300 blocks the current to the laser beam generating part 100 from the power supply part 400. Thus, the laser beam generating part 100 does not generate the single-color laser beam.

In the above state, when the probe 300a is pushed against the treatment object region 500 on the skin of a patient, the probe 300a goes down while depressing the skin. Thus, the switch part 300 is turned ON, so that current can be supplied to the laser beam generating part 100 from the power supply part 400. The laser beam generating part 100 supplied with the current generates a single-color laser beam of approximately 670 nm at a power level of 60 mW to 100 mW. The projecting part 200 condenses the single-color laser beam on the treatment object region 500 located in the focal plane. Thus, a pain due to inflammation of the treatment object region 500 is relaxed, so that analgesic, activation of cell and tissue, and immunity can be enhanced.

Retina disease which may be caused at an output level of 60 mW to 100 mW in LLLT can be avoided by preventing the single-color laser beam from being radiated to the outside of the projecting part 200 in such a manner that the probe 300a of the switch part 300 is pushed against the treatment object region 500. Thus, it is possible to prevent the single-color laser beam emitted by the laser beam generating part 100 from being incident to an eye of the patient.

However, the conventional laser beam treatment apparatus thus constructed has a disadvantage in that the probe 300a of the switch 300 must be continuously pushed against the treatment object region 500 onto which the single-color laser beam is to be projected. Thus, in a case where the treatment object region 500 is an exposed wounded skin part (for example, herpes zoster with a water blister, a burn or scald), LLLT cannot be employed.

Particularly, since the laser beam used in LLLT is a single-color light, the light must be set at an output level of 60 mW to 100 mW, which may, however, cause retina disease.

The probe 300a of the switch part 300 is pushed against the treatment object region 500 onto which a spot of the single-color laser beam is projected. Thus, it is difficult to efficiently project the laser beam onto the treatment object region 500, if the region 500 is wide. Thus, treatment cannot be performed efficiently.

SUMMARY OF THE INVENTION

It is an object of the present invention to provide a laser beam treatment apparatus which has enhanced safety and enables efficient treatment in LLLT.

The above object of the present invention is achieved by a laser beam treatment apparatus including a laser beam generating part generating and emitting a plurality of laser beams of different colors, and a projecting part condensing the plurality of laser beams and projecting the laser beams onto a treatment object region. The laser beams can be emitted at a lower level than that used in the conventional apparatus. In this case, the laser beams of the different colors related to different physiological actions collaborate with each other, so that the effects brought by LLLT can be enhanced. The output level of the laser beams is as low as 5 mW, so that safety can be ensured.

The laser beam treatment apparatus of the invention may be configured so that the projecting part emits, for example, a laser beam of blue, a laser beam of green, and a laser beam of red. The laser beam of blue increases activity in the parasympathetic nervous system, and the laser beam of red increases activity in the sympathetic nervous system. The laser beam of green increases activity in adjustment of the balance between the parasympathetic nervous system and the sympathetic nervous system. Thus, it is possible to adjust the autonomic nervous system more effectively. That is, the laser beam of red increases activity in the sympathetic nervous system so that a tendency toward excitation is caused in a living body, whereas the laser beam of blue increases activity in the parasympathetic nervous system so that excitation of a living body can be suppressed. The laser beam of green has intermediate performance between the laser beams of red and blue, and acts on both the sympathetic nervous system and parasympathetic nervous system, so that the balance therebetween can be adjusted.

The laser beam treatment apparatus of the present invention may be configured as follows. The projecting part emits the laser beam of green at a constant reference output level, and emits the laser beams of red and blue so that the output levels of the red and blue laser beams vary oppositely with respect to the constant reference output level. Thus, the balance between the parasympathetic nervous system and the sympathetic nervous system can be adjusted by the laser beam of green emitted at the constant reference output level, while the laser beams of blue and red alternately stimulate the parasympathetic nervous system and the sympathetic nervous system. It is thus possible to rapidly and forcedly adjust the autonomic nervous system.

The laser beam treatment apparatus of the present invention may be configured so that the projecting part emits the laser beams of blue and red in a pulse-like formation in which the output levels thereof vary at a frequency of a few Hz to 1 kHz. It is therefore possible to accurately and rapidly perform the adjustment operation and to improve the treatment effects.

The laser beam treatment apparatus of the present invention may be configured so that the projecting part emits the laser beams of blue, green and red having the following wavelengths. The laser beam of blue has a wavelength of approximately 400 nm to 430 nm. The laser beam of green has a wavelength of approximately 530 nm. The laser beam of red has a wavelength of approximately 670 nm. By using the laser beams of blue, green and red having the respective particular wavelengths, it is possible to accurately and rapidly perform the adjustment operation and to improve the treatment effects.

The laser beam treatment apparatus of the present invention may be configured so that the projecting part emits the laser beams of different colors at a maximum output level of approximately 5 mW. With the above setting of the output level, it is possible to prevent retina disease and enhance safety and to improve the efficiency in treatment.

The laser beam treatment apparatus of the present invention may be configured so that the projecting part has a function of arbitrarily adjusting the condensing ranges of the laser beams at an outlet for the laser beams. Thus, it is possible to project the laser beams onto a target range in the treatment object region and improve the efficiency in treatment.

BRIEF DESCRIPTION OF THE DRAWINGS

Other objects, features and advantages of the present invention will become more apparent from the following detailed description when read in conjunction with the accompanying drawings, in which.

DESCRIPTION OF THE PREFERRED EMBODIMENTS (First Embodiment)

Figure 1A:
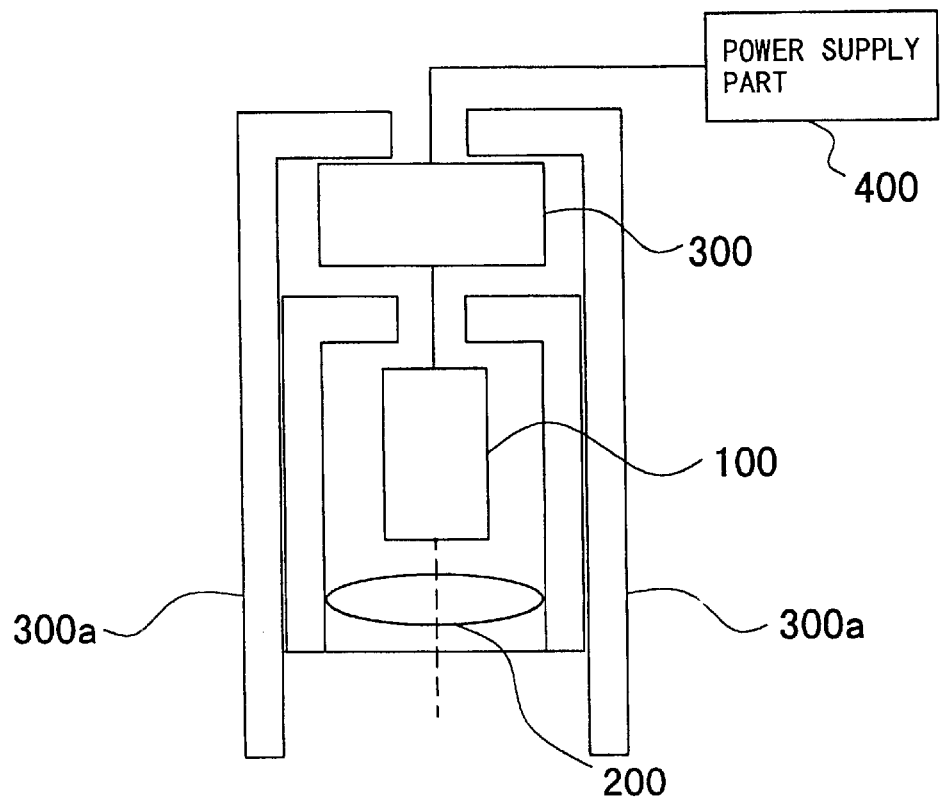
FIGS. 1A and 1B are block diagrams schematically illustrating the overall structure of a conventional laser beam treatment apparatus.
Figure 1B:
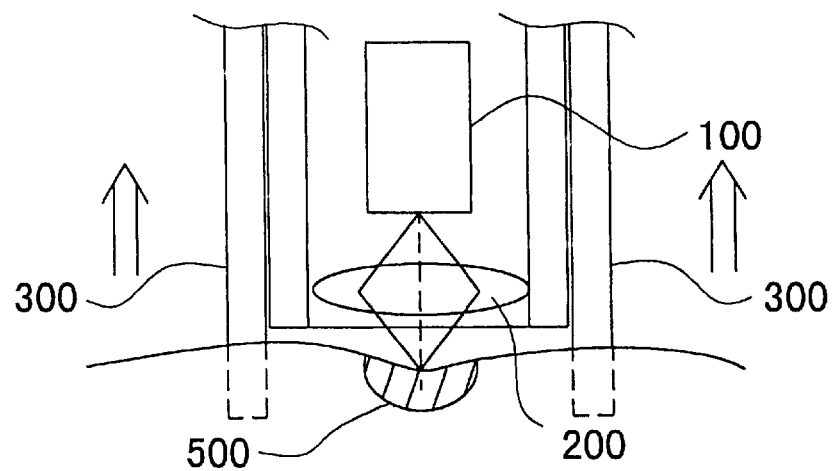
Figure 2:
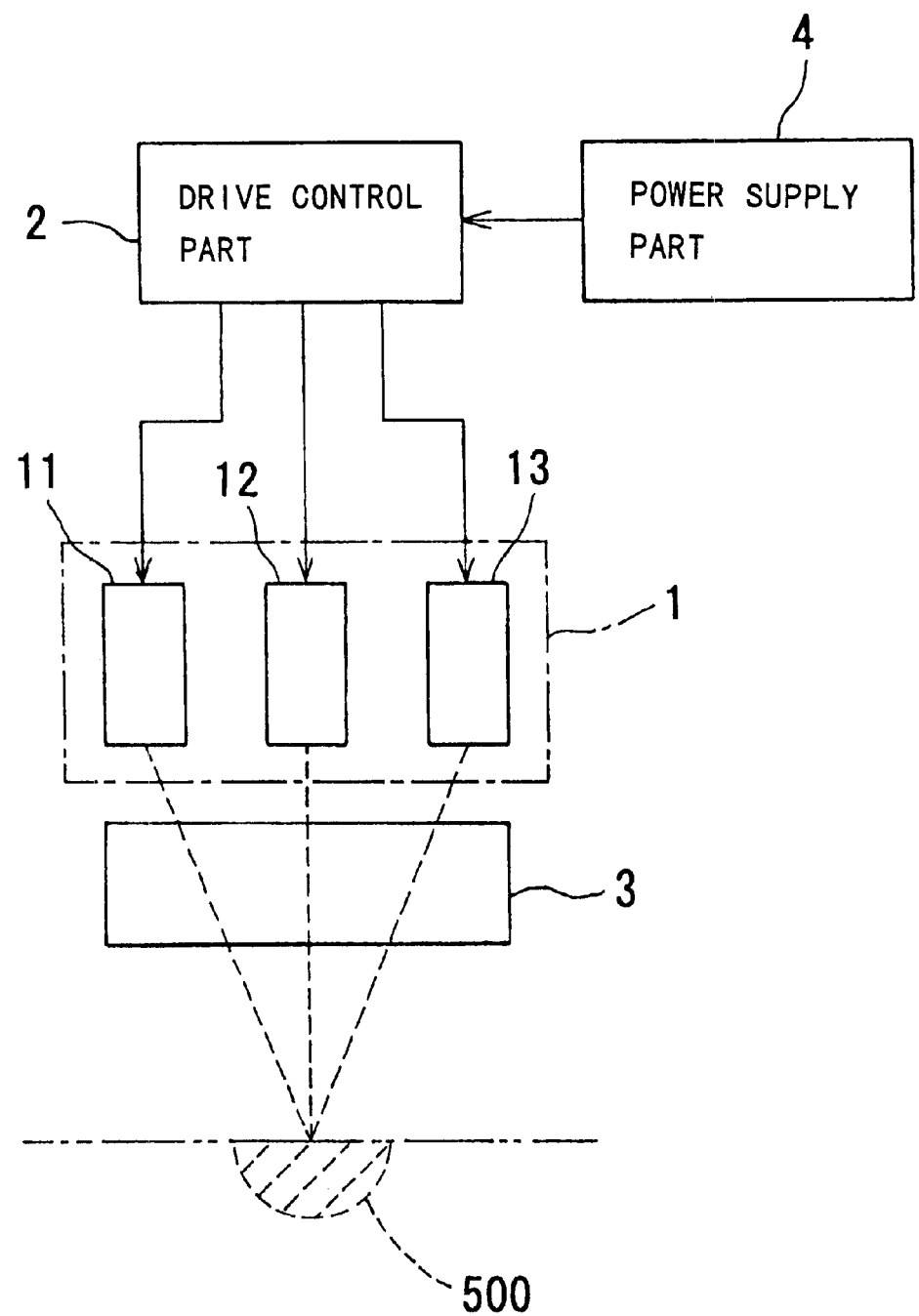
FIG. 2 is a block diagram schematically illustrating the overall structure of a laser beam treatment apparatus according to a first embodiment of the present invention.

A description will now be given, with reference to FIGS. 2 and 3, of a laser beam treatment apparatus according to a first embodiment of the present invention. FIG. 2 is a block diagram schematically illustrating the overall structure of the laser beam treatment apparatus, and FIG. 3 illustrates a change of the projection range with respect to a treatment object region.

Figure 3:
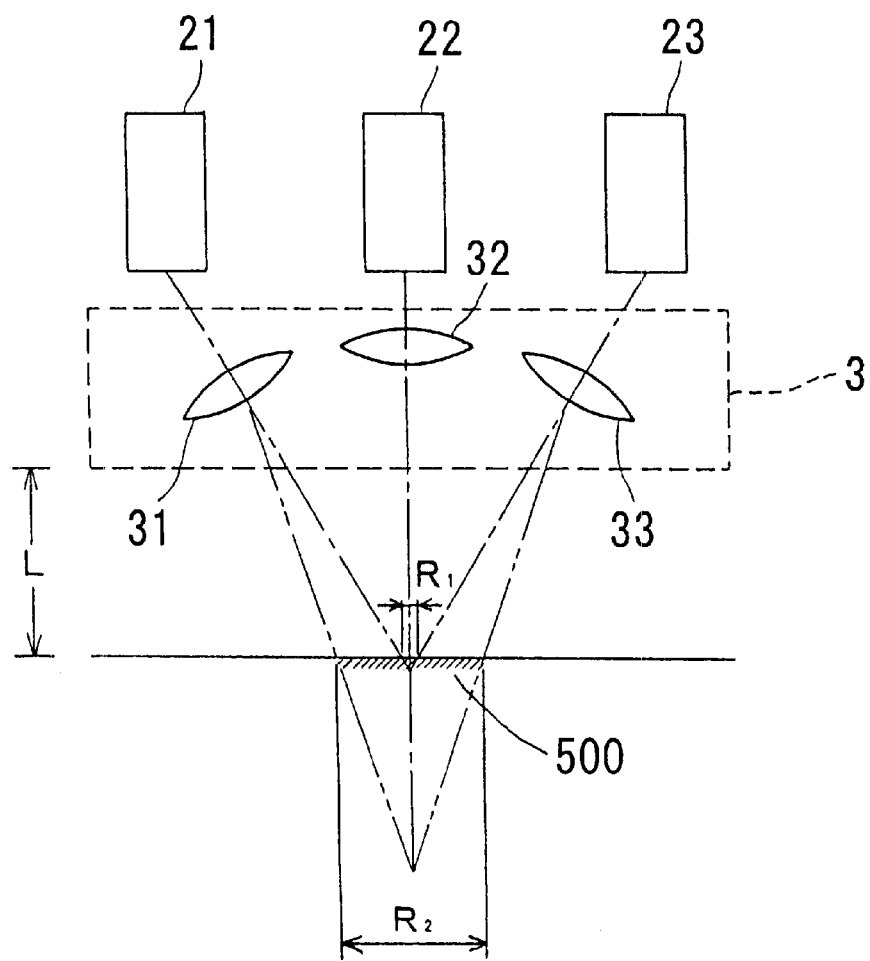
FIG. 3 illustrates a change of the projection range with respect to a treatment object region in the laser beam treatment apparatus shown in FIG. 2.

Referring to FIGS. 2 and 3, the laser beam treatment apparatus is made up of a laser beam generating part 1, a drive control part 2, a projecting part 3, and a power supply part 4. The laser beam generating part 1 generates laser beams of blue, green and red. The drive control part 2 controls the operation of the laser beam generating part 1. The projecting part 3 condenses the laser beams of blue, green and red emitted by the laser beam generating part 1 on the treatment object region 500 so that the condensed laser beams are projected onto the treatment object region 500. The power supply part 4 supplies the projecting part 3 with electricity, and supplies the laser beam generating part 1 with electricity via the projecting part 3.

The laser beam generating part 1 includes a blue laser 11, a green laser 12, and a red laser 13. The blue laser 11 emits a blue laser beam in a wavelength of approximately 430 nm. The green laser 12 emits a green laser beam in a wavelength of approximately 530 nm. The red laser 13 emits a red laser beam in a wavelength of approximately 670 nm. The lasers 11, 12 and 13 emit the laser beams of the respective colors at a maximum output level of approximately 5 mW.

The projecting part 3 is equipped with optical systems 31, 32 and 33, which respectively condense the blue, green and red laser beams at the same point. The optical systems 31, 32 and 33 have the function of changing the focal depths, so that the projection area on the treatment object region 500 can be adjusted. The focal depths of the optical systems 31, 32 and 33 can be adjusted manually or automatically by a control operation of the drive control part 2.

A description will be given of a treatment operation of the laser beam treatment apparatus according to the first embodiment of the present invention. The blue, green and red lasers 11, 12 and 13 of the laser beam generating part 1 emit the blue, green and red laser beams under the control of the drive control part 2 in a state in which the projecting part 3 is spaced apart from the treatment object region 500 at a distance L.

The blue, green and red laser beams are condensed and projected onto the treatment target region 500 due to the function of the optical systems 31, 32 and 33 of the projecting part 3, respectively. The condensed red laser beam stimulates the sympathetic nervous system in such a way as to have a tendency toward excitation, so that a blood expanding action can be caused to improve circulation of the blood. The condensed blue laser beam stimulates the parasympathetic nervous system in such a way as to have a tendency toward excitation, so that electrical excitation in the cell films of the nervous system involved in a sense of pain. The condensed green laser beam functions to balance the sympathetic nervous system and the parasympathetic nervous system. It has been observed by thermographs that improvement in circulation of the blood acts to raise the temperature of a region of chronic pain and to decrease the temperature of an acute inflammation region.

As described above, the laser beams of blue, green and red act on the treatment object region 500 and collaborate thereon with one another so that the treatment effects can be improved.

(Second Embodiment)

A description will now be given of a laser beam treatment apparatus according to a second embodiment of the present invention by referring to FIGS. 2 and 3. FIG. 3 shows output level characteristics of blue, green and red laser beams of the laser beam treatment apparatus according to the second embodiment of the present invention.

The laser beam treatment apparatus is equipped with the laser beam generating part 1, the drive control part 2, the projecting part 3, and the power supply part 4, as in the case of the first embodiment of the present invention. However, the drive control part 2 used in the second embodiment controls the laser beam generating part 1 in a way different from that used in the first embodiment. As shown in FIGS.

Figure 4A:
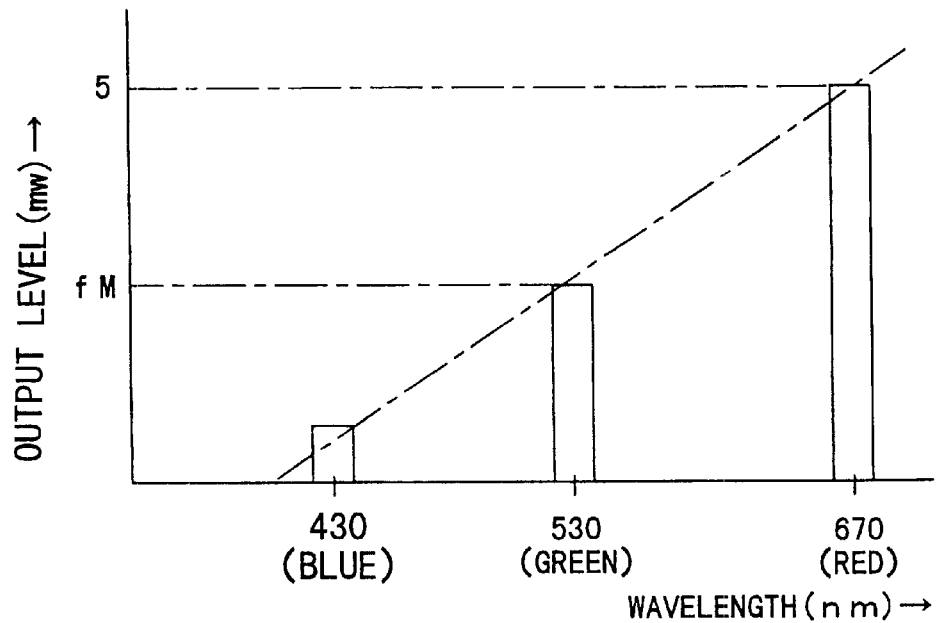
FIGS. 4A and 4B are graphs of output level characteristics of blue, green and red laser beams used in a laser beam treatment apparatus according to a second embodiment of the present invention.
Figure 4B:
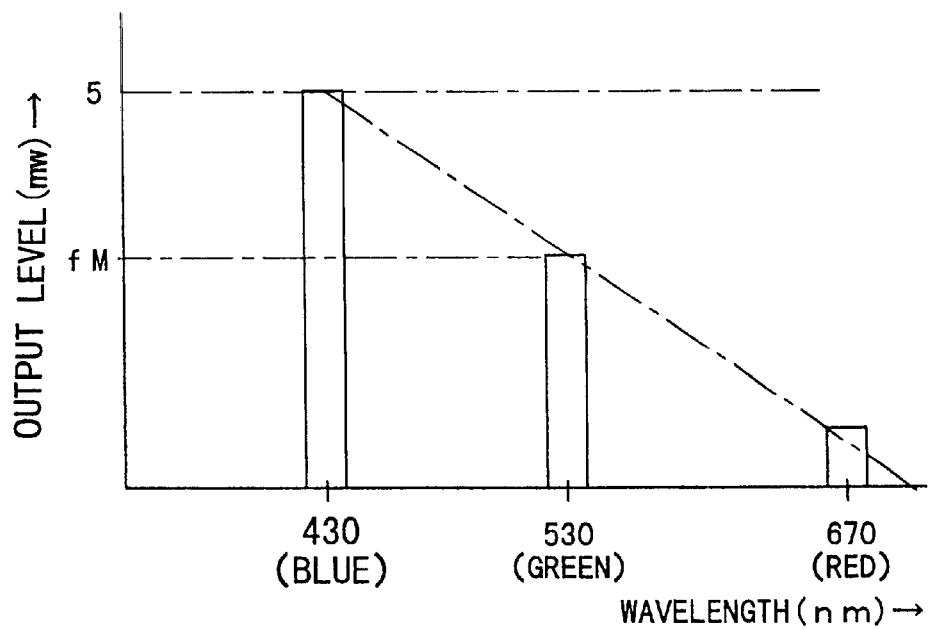

4A and 4B, the green laser beam emitted by the green laser 12 of the laser beam generating part 1 is arranged so as to have a constant reference output level fM. The blue and red laser beams respectively emitted by the blue laser 11 and the red laser 13 are arranged so as to have output levels which vary oppositely along the vertical axis with respect to the reference output level fM. In FIG. 4A, the output levels of the red and blue laser beams are respectively higher and lower than the reference output level fM. In FIG. 4B, the output levels of the blue and red laser beams are respectively higher and lower than the reference output level fM.

The output levels of the blue and red laser beams can be varied within the maximum range of about 5 mW, and the periods of variations in the output levels thereof can arbitrarily be adjusted so as to be suitable for a symptom of a patient. The blue and red laser beams can arbitrarily be varied within a variation range of 1 to 5 mW. The blue and red laser beams can be varied so that the beams are output in a pulse-like formation at a frequency of a few Hz to 1 kHz. The following have been observed. A variation period of about 10 Hz is sufficient to a light wound. A variation period of about 100 Hz results in great effects for a medium wound. A variation period of about 1000 Hz results in great effects for a serious wound.

It is also possible to select one of the red and blue laser beams so as to have a larger (or smaller) variation width than the other one, taking into consideration the symptom of the treatment object region 500. For example, in a case where it is necessary to stimulate the parasympathetic nervous system of a patient toward excitation more strongly (weakly) than the sympathetic nervous system, the red laser beam (blue laser beam) is adjusted so as to have a greater variation width than that of the other one.

The reference output level fM of the green laser beam may be set equal to half the maximum output level (for example, 5 mW) of the blue or red laser beam, namely, to 2.5 mW. However, the reference output level fM may be set to an arbitrary value between 0 mW and the maximum output level. For example, if a symptom of a patient needs the balance between the sympathetic nervous system and the parasympathetic nervous system, the reference output level fM of the green laser beam may be set close to the maximum value.

The embodiments of the present invention described above employ the laser beams of different colors emitted by the laser beam generating part 1. Alternately, it is possible to employ light-emission diodes that emit different colors of lights.

The projecting part 3 in each of the above-mentioned embodiments of the present invention condenses and projects the laser beams of blue, green and red in the same direction by the optical systems 31, 32 and 33. Alternatively, it is possible to form the optical systems 31, 32 and 33 by optical fibers so that ends of the optical fibers are arranged close to each other so as to condense the laser beams. The laser beams of blue, green and red emitted by the laser beam generating part 1 are propagated through the optical fibers and are condensed and projected onto the treatment object region 500.

It is also possible to employ a single optical fiber through which the laser beams of blue, green and red are propagated and are condensed and projected onto the treatment object region 500.

A further description will be given of the present invention by referring to cases which are treated by the low-reactive level laser therapy (LLLT) to which the present invention is applied.

As the first example, the blue, green and red laser beams were condensed and projected onto a wounded surface of a herpes zoster having a water blister, which is expected to be treated in such a way that the probe is pushed against the wounded surface. A pain was reduced one minute after the treatment was initiated and was removed by five minutes. The above treatment was performed day after day for patients. Pains of the patients completely were removed by one day to five days and the wounds were healed. There was no case that a pain-after-herpes-zoster, which is said to be an intractable disease, occurred. Further, the inventor treated 11 cases in which patients had symptoms similar to the above-mentioned symptom and obtained similar effects by the treatment.

Next, as the second example, patients having periarthritis scapulohumeralis, lumbago, and knee joint disease (five males and five females for each of the diseases) were treated by using the laser beam treatment apparatus of the present invention in such a way that the blue, green and red laser beams are condensed and projected onto the treatment target regions for five minutes at one time and this operation was repeated ten times. The pain relief score (PRS) was counted before and after the treatment. In the PRS, a pain before treatment is assigned a score of 10 points. The patients are asked of the score corresponding to the current pain after treatment. The score after treatment is indicative of the effects of treatment. The PRS is widely used to evaluate the effects of pain treatment.

The scores after the treatment using the laser beam treatment apparatus of the invention were reduced to 7.8, 8.8, and 8.0 for periarthritis scapulohumeralis, lumbago, and knee joint disease, respectively. These scores are superior to those reported by treatment using the conventional laser beam treatment apparatus.

Further, as the third example, patients having nasal blockage, nasal discharge, pain in the throat, and headache, which are symptoms of a cold, were treated using the laser beam treatment apparatus in such a way that the laser beams are condensed and projected, for one minute, onto each of the right and left portions of the ganglion stellatum which is sympathetic ganglia of the front cervical portion. The treatment resulted in improvements or disappearance of the symptoms. Further, the inventor treated 15 cases in which patients had symptoms similar to the above-mentioned symptoms and obtained similar effects by the treatment. Remarkable improvements in acute symptoms have not been confirmed in the conventional low-output laser beam treatment apparatus and are therefore considered as unique effects resulting from enhancement of balancing between the sympathetic nervous system and the parasympathetic nervous system by the present invention.

As the fourth example, an experiment was conducted which is directed to a clinical in which the following first and second different treatments are compared with each other. In the first treatment, the blue and red laser beams were alternately projected. In the second treatment, the laser beam of green, which is an intermediate color between blue and red, was projected at the constant reference output level fM, while the red and blue laser beams were alternately projected.

The experimental results showed the following. The first treatment brought effectiveness higher than that brought by projection of a single-color laser beam. The second treatment using the green laser beam brought very higher effectiveness. The above experimental results are satisfactory due to the fact that the green laser beam enhances the balancing between the sympathetic nervous system and the parasympathetic nervous system.

The green laser beam was effective to a pain. However, very higher effectiveness was obtained by using the laser beams of the three colors. It is supposed that the process of alternately projecting the blue and red laser beams, which alternately stimulate the sympathetic and parasympathetic nervous systems respectively, while projecting the green laser beam at the constant reference output level fM, acts on balancing of the automatic nervous system of a living body very effectively.

The present invention is not limited to the specifically disclosed embodiments, and variations and modifications may be made without departing from the scope of the invention.

What is claimed is:

1. A laser beam treatment apparatus comprising:
   a laser beam generating part generating and emitting a plurality of laser beams of different colors; and
   a projecting part condensing the plurality of laser beams and projecting the laser beams onto a treatment object region,
   wherein said plurality of laser beams include a first laser beam at a first wavelength, a second laser beam at a second wavelength different from said first wavelength, and a third laser beam at a third wavelength different from said first and second wavelengths,
   said projecting part emitting said first laser beam at a constant output reference level, and emitting said second and third laser beams so that output levels of said second and third laser beams vary oppositely with respect to said constant reference output level.

2. The laser beam treatment apparatus as claimed in claim 1, wherein said projecting part emits a blue laser beam, a green laser beam, and a red laser beam.

3. A laser beam treatment apparatus comprising:
   a laser beam generating part generating and emitting a plurality of laser beams of different colors; and
   a projecting part condensing the plurality of laser beams and projecting the laser beams onto a treatment object region,
   wherein said projecting part emits a blue laser beam, a green laser beam, and a red laser beam,
   wherein said projecting part emits the green laser beam at a constant output level, and emits the blue and red laser beams so that output levels of the blue and red laser beams vary oppositely with respect to the constant reference output level.

4. The laser beam treatment apparatus as claimed in claim 3, wherein the projecting part emits the blue and red laser beams in a pulse-like formation in which the output levels of the blue and red laser beams vary at a frequency of a few Hz to 1 kHz.

5. The laser beam treatment apparatus as claimed in claim 2, wherein the projecting part emits the blue laser beam of a wavelength of approximately 400 nm to 430 nm, the green laser beam of a wavelength of approximately 530 nm, and the red laser beam of a wavelength of approximately 670 nm.

6. The laser beam treatment apparatus as claimed in claim 1, wherein the projecting part emits the laser beams of different colors at a maximum output level of 5 mW.

7. The laser beam treatment apparatus as claimed in claim 1, wherein the projecting part includes a part that adjusts projection ranges of the laser beams of said different colors.

8. The laser beam treatment apparatus as claimed in claim 2, wherein the projecting part emits the laser beams of different colors at a maximum output level of 5 mW.

9. The laser beam treatment apparatus as claimed in claim 2, wherein the projecting part includes a part that adjusts projection ranges of the laser beams of different colors.

10. The laser beam treatment apparatus as claimed in claim 1, wherein the projecting part comprises optical fibers through which the plurality of laser beams are respectively propagated, ends of the optical fibers being close to each other so as to condense and project the laser beam onto the treatment object region.

11. The laser beam treatment apparatus as claimed in claim 1, wherein the projecting part emits the blue and red laser beams in a pulse-like formation in which the output levels of the blue and red laser beams vary at a frequency of a few Hz to 1 kHz.

12. The laser beam treatment apparatus as claimed in claim 1, wherein said treatment object region is located on a patient.

13. The laser beam treatment apparatus as claimed in claim 1, wherein said plurality of laser beams are projected onto a projection area of said treatment object region, said projecting part adjusting said projection area.

14. The laser beam treatment apparatus as claimed in claim 1, wherein said laser beam treatment apparatus provides treatment therapy to a patient.

15. The laser beam treatment apparatus as claimed in claim 3, wherein the projecting part emits the blue laser beam of a wavelength of approximately 400 nm to 430 nm, the green laser beam of a wavelength of approximately 530 nm, and the red laser beam of a wavelength of approximately 670 nm.

16. The laser beam treatment apparatus as claimed in claim 3, wherein the projecting part emits the laser beams of different colors at a maximum output level of 5 mW.

17. The laser beam treatment apparatus as claimed in claim 3, wherein the projecting part includes a part that adjusts projection ranges of the laser beams of said different colors.

18. The laser beam treatment apparatus as claimed in claim 3, wherein the projecting part emits the laser beams of different colors at a maximum output level of 5 mW.

19. The laser beam treatment apparatus as claimed in claim 3, wherein the projecting part comprises optical fibers through which the plurality of laser beams are respectively propagated, ends of the optical fibers being close to each other so as to condense and project the laser beams onto the treatment object region.

20. The laser beam treatment apparatus as claimed in claim 3, wherein said treatment object region is located on a patient.

21. The laser beam treatment apparatus as claimed in claim 3, wherein said plurality of laser beams are projected onto a projection area of said treatment object region, said projecting part adjusting said projection area.

22. The laser beam treatment apparatus as claimed in claim 3, wherein said laser beam treatment apparatus provides treatment therapy to a patient.

* * * * *